United States Patent [19]
Brown

[11] Patent Number: 5,918,603
[45] Date of Patent: Jul. 6, 1999

[54] METHOD FOR TREATING MEDICAL CONDITIONS USING A MICROPROCESSOR-BASED VIDEO GAME

[75] Inventor: Stephen J. Brown, San Mateo, Calif.

[73] Assignee: Health Hero Network, Inc.

[21] Appl. No.: 08/857,187

[22] Filed: May 15, 1997

Related U.S. Application Data

[62] Division of application No. 08/247,716, May 23, 1994, Pat. No. 5,678,571.

[51] Int. Cl.[6] .................................................. A61B 19/00
[52] U.S. Cl. .................................... 128/897; 128/905
[58] Field of Search ........................... 128/897–98, 668, 128/905; 600/481, 300

[56] References Cited

U.S. PATENT DOCUMENTS 5,307,263  4/1994  Brown .
5,678,571  10/1997  Brown .................................... 128/898

*Primary Examiner*—John P. Lacyk
*Attorney, Agent, or Firm*—Hopgood, Calimafde, Kalil & Judlowe, LLP

[57] ABSTRACT

Method for treating a medical condition in a human patient comprising choosing a psychological strategy for treating the medical condition, encoding electronic instructions for an interactive video game in such a way that the interactive video game implements the psychological strategy, loading the electronic instructions into a microprocessor-based unit (10, 30) equipped with a display (14, 34) for displaying the interactive video game and with an patient input device (16, 36a, 36b, 36c, 36d, 36e) for receiving responses to the interactive video game from the human patient, and instructing the human patient how and when to use the microprocessor-based unit (10) to play the interactive video game. The interactive video game contains instructions for a scoring procedure for quantitatively analyzing the medical condition of the human patient, and/or counseling instructions or self-care instructions. The video game can be used in conjunction with a physical parameter measuring device (54) connected to the microprocessor-based unit (10).

14 Claims, 14 Drawing Sheets

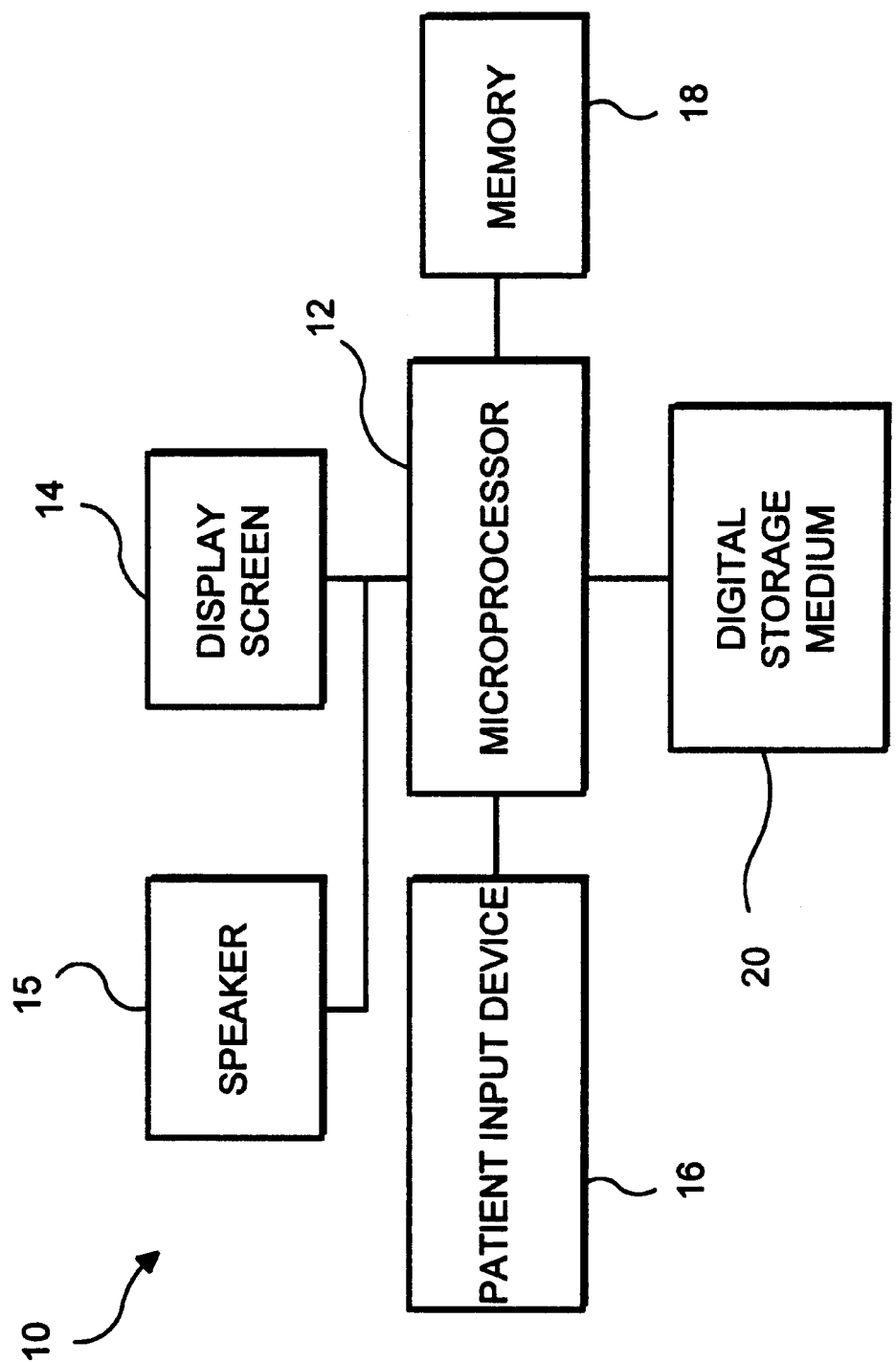
F I G. 1

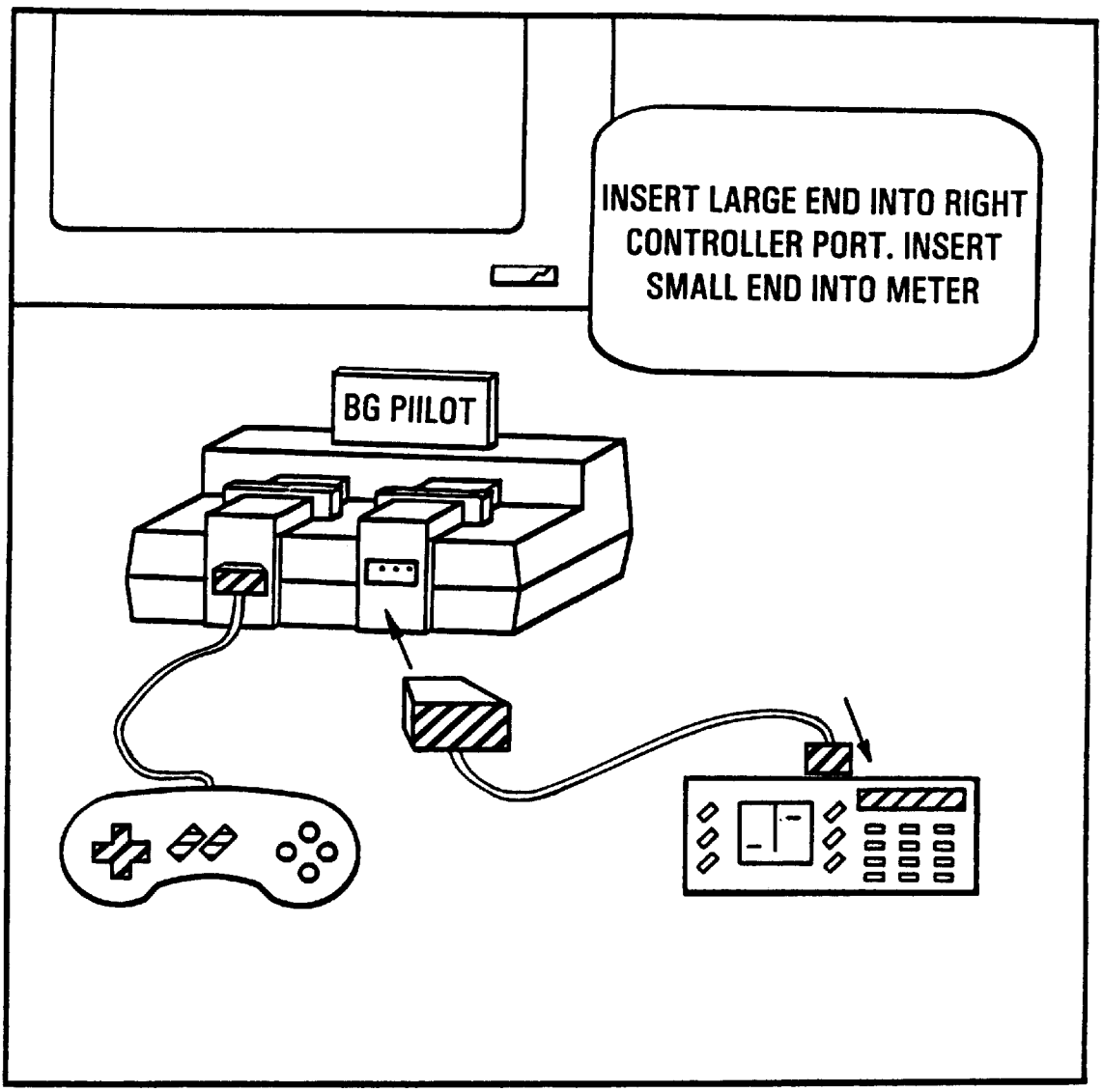
F I G. 9

METHOD FOR TREATING MEDICAL CONDITIONS USING A MICROPROCESSOR-BASED VIDEO GAME

This is a division of application Ser. No. 08/247,716, filed May 23, 1994, which is now U.S. Pat. No. 5,678,571.

BACKGROUND

1. Field of the Invention

The present invention relates to the field of medical treatment, and in particular to the treatment of medical conditions in human patients with the aid of a microprocessor-based video game.

2. Description of the Prior Art

Medical conditions associated with a patient's behavior pattern or well-being are typically evaluated and treated in therapy sessions conducted by a physician or a health care specialist. Depending on the ailment, a preliminary picture of the patient's condition may be available to the specialist in the form of answers to questionnaires or results of a battery of tests. This applies to psychological conditions such as schizophrenia, depression, hyperactivity, phobias, panic attacks, anxiety, overeating, and other psychological disorders. In fact, the number of diagnostic tests presently available for classifying these conditions is vast. Such tests rely on the patient to perform a self-examination and to respond candidly to a series of personal questions. Since most tests differ in their basic scientific assumptions the results obtained are not standardized and can not often be used to make meaningful case comparisons.

Consequently, the above-mentioned psychological conditions are fully diagnosed and treated in therapy sessions. In these settings the specialist can better evaluate the state of his patient and design appropriate, individualized treatment. Unfortunately, because of the amount of time required to do this, diagnosis and treatment are very expensive.

The actual therapeutic changes in the patient occur outside of therapy as the patient applies cognitive and behavioral strategies learned in therapy to problems encountered in day-to-day situations. Progress is predicated to a large extent on patient cooperation, discipline, and self-management. Diaries are employed to ensure patient compliance. Still, in many instances, lack of compliance to long-term therapy regimes presents a major obstacle to successful treatment. Children are a particularly difficult group of patients in this respect. Frequently, they lack the understanding, maturity, and perseverance required to successfully pursue a treatment plan.

In fact, it has recently been confirmed that in the case of anxiety the best treatment involves teaching the patients new ways of responding to old stimuli. Drugs may be used to blunt the physical aspects, but there is no data to confirm the positive effects of their long-term use. Meanwhile, treatment of depressions requires attentive counseling and listening to the patient. The same applies to treatment of personality disorders, obsessive-compulsive disorders, hysteria, and paranoia. Unfortunately, cost of treatment and compliance with suggestions made by the therapist are major problems, as pointed out above.

In difficult cases observation and comparison with criteria compiled in the Diagnostic and Statistical Manual of Mental Disorders—the standard classification text of the American Psychiatric Association—are the only recognized treatment alternatives.

There is also a wide variety of medical conditions, other than the above-mentioned psychological disorders, requiring extensive self-help and self-treatment by the patient. These conditions include addictions, compulsive behaviors, and substance abuse. Most common examples are smoking, gambling, and alcoholism. At the present time treatment for these medical conditions involves counseling, distraction techniques, and chemical replacement therapy. Ultimately, however, all of these methods depend on the cooperation of the patient and a large dose of self-motivation. This is especially important when the patient is in his or her own surroundings where the objects of their addition or compulsion are easily accessible.

Unfortunately, compliance with medical advice is notoriously poor, and gentle persistence may be necessary. Some physicians recommend that the entire family or other group of significant personal contracts in the patient's life should be involved with the patient's consent. This, of course, presents major problems and is a costly treatment method.

Some attempts have been made at using computers to diagnose and educate patients about their medical condition. Typically, these attempts have produced questionnaires which can be filled out on a computer, or educational programs telling the patient more about his or her medical condition. Unfortunately, these projects stop short of being sufficiently adapted to patient needs to help with treatment or therapy. In fact, health care professionals maintain that computers can never replace the sense of caring, of relatedness, which is the vehicle in which most therapy takes place.

OBJECTS AND ADVANTAGES OF THE INVENTION

In view of the above, it is an object of the present invention to provide a method for treating a medical condition by using a microprocessor-based video game to produce a better preliminary picture of the ailment, make therapy considerably less costly, and emphasize superior patient self-help responses.

Other objects of the invention are to enable treatment in the patient's own, private environment, provide a treatment method to which the patient can resort as the need arises, and ensure higher treatment compliance for all patients, and in particular children.

Finally, it is another object to provide a better method for standardization of treatment results for psychological disorders.

These and other objects and advantages will become more apparent after consideration of the ensuing description and the accompanying drawings.

SUMMARY OF THE INVENTION

Surprisingly, it has been found that in the case of psychological disorders, addictions, substance abuse, and compulsions one can successfully use treatment methods based on computer-generated video games. Such method for treating a medical condition in a human patient comprises the steps of: choosing a psychological strategy for treating the medical condition, encoding electronic instructions for an interactive video game in such a way that the interactive video game implements the psychological strategy, loading the electronic instructions into a microprocessor-based unit equipped with a display for displaying the interactive video game and with a patient input device for receiving responses to the interactive video game from the human patient, and instructing the human patient how and when to use the microprocessor-based unit to play the interactive video game.

The psychological strategy implemented by the interactive video game can involve a graphical game character faced with fictitious challenges representative of the patient's medical condition. The responses of the human patient to these challenges of the graphical game character can define the game success of the graphical game character. Moreover, the interactive video game can contain instructions for a scoring procedure for quantitatively analyzing the medical condition of the human patient. This enables a health specialist to draw comparisons between results obtained for different patients.

Besides psychological strategies the video game can also contain counseling instructions or self-care instructions. In fact, the video game can be used in conjunction with a standard monitoring device. To do this a monitoring device for measuring a physical parameter, e.g., blood glucose level for a patient with diabetes, is connected to the microprocessor-based unit. Then a second set of electronic instructions is encoded for operating said monitoring device, where the second set of electronic instructions is compatible with the first set of electronic instructions. Finally, the two sets of instructions are merged.

BRIEF DESCRIPTION OF THE DRAWINGS

FIG. 1 is a block diagram of an autonomous computer system employed in the method according to the invention.

FIG. 9 is still another exemplary screen for the video game of FIG. 7.

Figure 2:
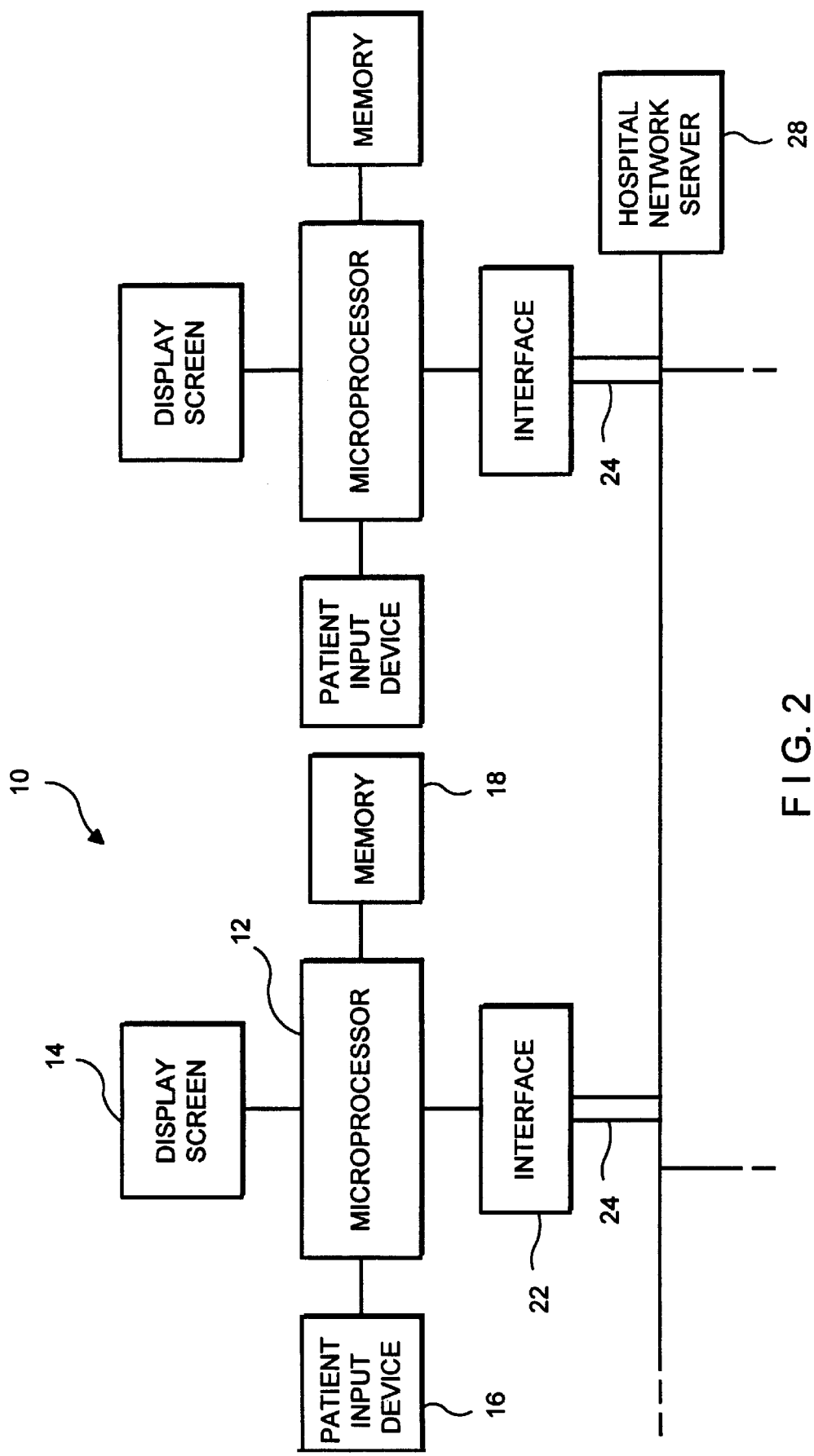
FIG. 2 is a block diagram of a computer network used in the method according to the invention.
Figure 3:
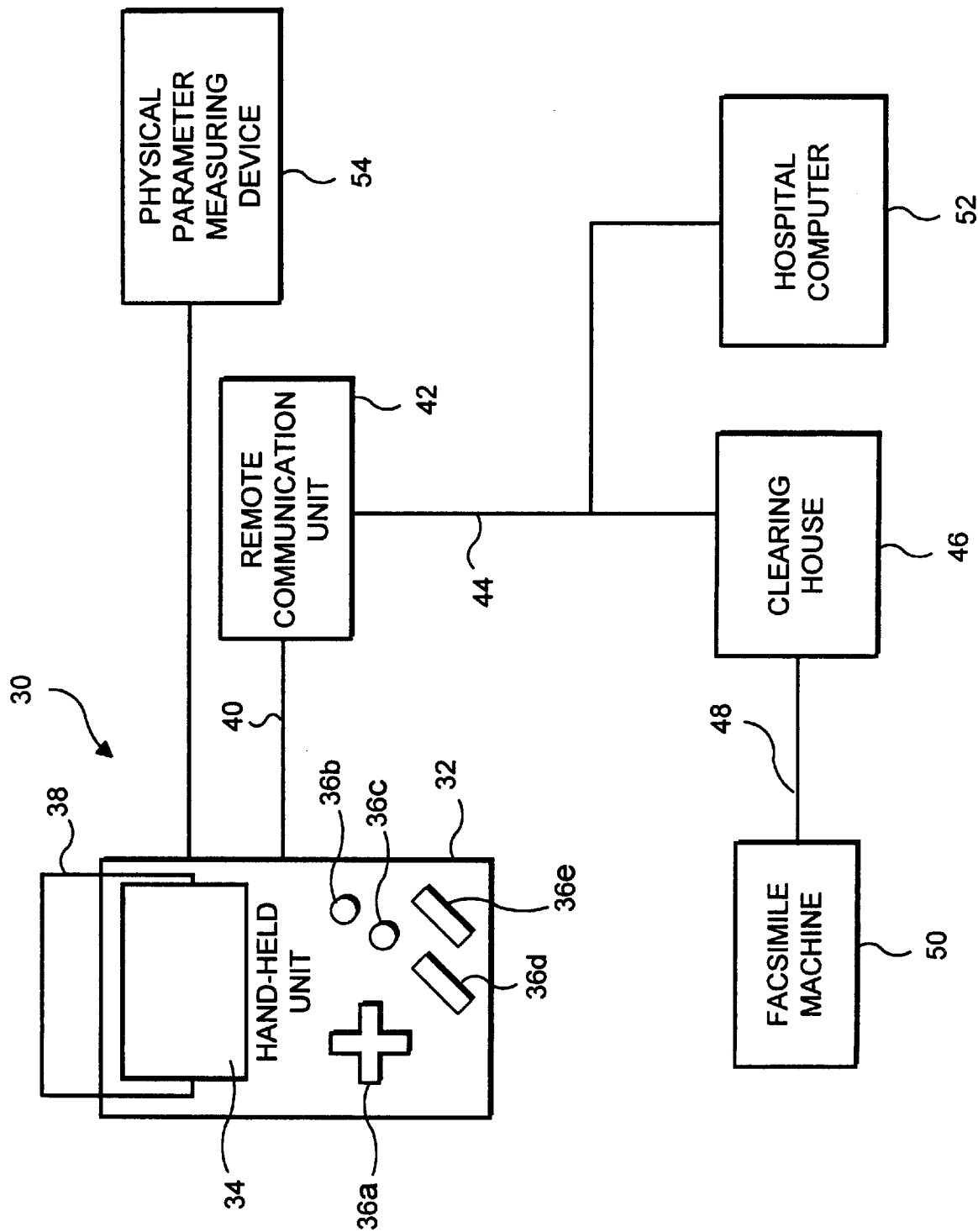
FIG. 3 is a block diagram of a system employing a hand-held microprocessor unit for implementing the method of the invention.

DESCRIPTION OF PREFERRED EMBODIMENTS—FIGS. 1 to 3

FIG. 1 shows a block diagram representing a typical embodiment of a computer or microprocessor-based unit 10 capable of supporting video games for patient treatment. At the heart of unit 10 is a microprocessor 12. In addition to operations necessary to run unit 10, microprocessor 12 can process video data. Of course, in complicated systems the tasks of microprocessor 12 can be performed by a number of microprocessors. In the most preferred embodiment microprocessor 12 is a SUPER NINTENDO™ microprocessor.

A display unit or screen 14 is connected to microprocessor 12. The resolution and size of display screen 14 are sufficient to project visual images generated by video games. In a preferred embodiment screen 14 is a high-resolution video monitor or television screen. A speaker 15 for producing sounds associated with video games is hooked up to microprocessor 12 as well.

A patient input device 16 is also connected to microprocessor 12. Input device 16 can be a keyboard, joystick, mouse, button, trigger, light-pen, or the like, or combinations of these devices. A suitable choice of input device 16 is made based on the video game displayed on display screen 14 and the medical conditions of the human patient. The selected input device 16 will thus permit the patient to actively participate in the video game.

Additionally, microprocessor-based unit 10 has a memory 18, which is in communication with microprocessor 12. Memory 18 contains data required by microprocessor 12 to operate unit 10. While in the exemplary embodiment illustrated in FIG. 1 memory 18 consists of a single unit, configurations with many memory units of different types are possible.

Unit 10 is also connected to a digital storage medium 20 and appropriate data reading devices (not shown). Digital storage medium 20 can be a hard-disk, a floppy disk, a compact disk (CD), a cartridge, a network storage unit, or any other convenient medium capable of storing electronic instructions for running a video game on unit 10. In the preferred embodiment storage medium 20 is a high-storage-capacity CD disk. The ability to hold a large amount of data is a prerequisite for storing large video game programs.

FIG. 2 is a block diagram of a computer network for practicing the video game treatment method. Individual microprocessor-based units 10 on the computer network are substantially the same as in FIG. 1, therefore the same reference numbers are used for corresponding parts. Instead of digital storage medium 20, units 10 in FIG. 2 have a network interface 22 equipped with a network link 24. Link 24 connects microprocessor 12 to network 26 via interface 22. In a preferred embodiment network 26 is a separate hospital network adapted to patient use.

On the hospital side network 26 is connected to a hospital network server 28. Server 28 is capable of exchanging data, in particular video game data, with each unit 10 connected to network 26. Server 28 is also connected to computers used by monitoring personnel and physicians at the hospital (not shown).

The block diagram of FIG. 3 shows a particularly convenient embodiment for implementing the diagnosis and treatment method. A hand-held microprocessor unit 30 is equipped with a video display 34 and a number of input switches or keys 36a, 36b, 36c, 36d, and 36e, which are mounted on a housing 32. A set of components including a microprocessor, memory circuits, and circuitry that interfaces keys 36a, 36b, 36c, 36d, and 36e with the microprocessor is installed inside housing 30 but not shown in FIG. 3. Stored in the memory of programmable hand-held microprocessor unit 30 is a set of electronically encoded program instructions. These instructions establish a data protocol that allows hand-held microprocessor unit 30 to perform digital data signal processing and generate desired data or graphics for display on display unit 34 when a program cartridge 38 is inserted into a slot or other receptacle in housing 32. That is, cartridge 38 of FIG. 3 includes read-only memory data encoding the instructions for playing a particular video game.

In the most preferred embodiment hand-held microprocessor unit 30 is the compact game system manufactured by Nintendo of America, Inc. under the trademark "GAME BOY". This device is particularly simple. Furthermore, unit 30 is hooked up to a remote communication unit 42 via a connection cable 40. Preferably, for reasons of convenience, unit 42 can be a modem capable of communicating over telephone lines, or a radio-frequency transceiver capable of wireless sending and receiving of information. Of course, any other common telecommunications devices can also be used. It is assumed in the preferred embodiment shown in FIG. 3 that unit 42 is a high-speed modem.

A communication line 44, in this event a telephone line, connects unit 42 to a data clearing house 46 and hospital computer 52. This set-up establishes an efficient data pathway from hand-held microprocessor unit 30 to clearing house 46 and hospital computer 52. Clearing house 46 is capable of classifying data and sending appropriate messages concerning the patient's medical condition to a health care professional or physician. In the preferred embodiment clearing house 46 is connected by transmission line to a facsimile machine 50 standing in the office of a physician or health care professional.

A physical parameter measuring device 54, e.g., a glucose blood meter or a respiratory flow meter is also connected to hand-held unit 30. Device 54 is designed for patient self-monitoring while playing a video game. For this purpose device 54 is capable of downloading measurement data into hand-held unit 30. Appropriate choice of device 54 is made by the physician depending on the other hardware and intended video game for patient treatment.

OPERATION—FIGS. 1 to 10

Figure 4:
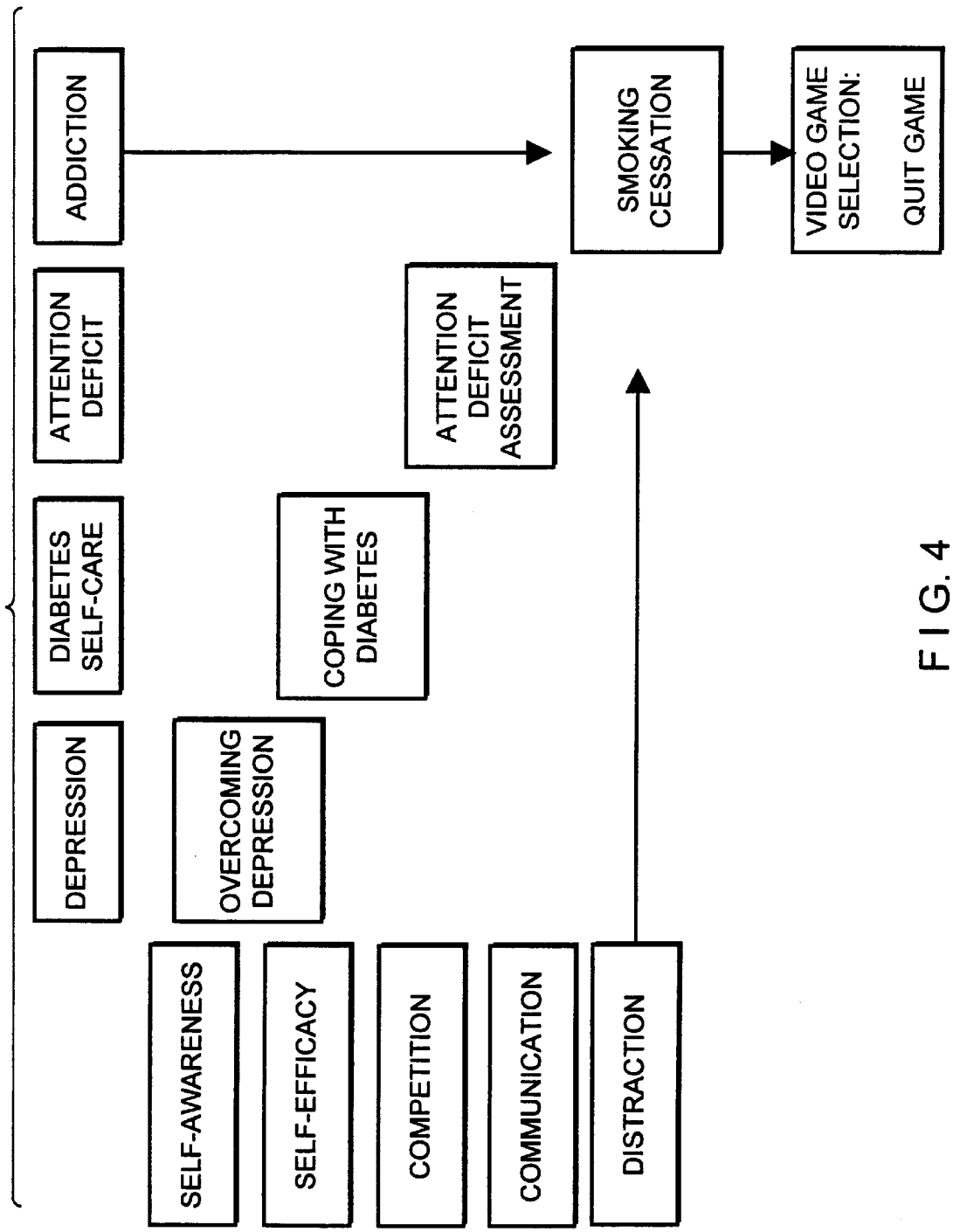
FIG. 4 is a flow chart illustrating how to select an appropriate video game treatment for some common medical conditions.

Before using microprocessor-based unit 10 shown in FIG. 1, a patient will first visit a physician or health care professional to evaluate his or her medical condition. The physician will diagnose the condition and choose the proper treatment based on patient needs. The flow chart in FIG. 4 shows the psychological strategies which the physician can select for treating depression, attention deficit, addiction, and diabetes. The psychological strategies listed include self-awareness training, self-efficacy training, competition, communication, and distraction. Of course, other well-known strategies such as positive reinforcement, negative reinforcement, role-playing, etc. can be employed as well. In addition to these, the psychological treatment strategy can include counseling methods and self-care instructions. Moreover, the treatment strategies can be combined as shown. For example, as shown in FIG. 4, overcoming depression is best ensured by a therapy which joins self-awareness training with learning self-efficacy to regain control over one's life. In the particular case highlighted with two arrows the medical condition to be treated is an addiction, e.g., smoking or alcoholism, and the appropriate psychological strategy for treating this condition is distraction.

Once the psychological treatment strategy has been selected, the physician will choose an appropriate interactive video game program comprising this strategy. Examples of video games based on the most common psychological strategies will be given in the specific examples to follow. Meanwhile, the program itself consists of electronically encoded instructions in data storage medium 20 (FIG. 1). The video game program is loaded from this medium 20 into microprocessor 12 and memory 18 of unit 10. In the preferred embodiment this is accomplished most conveniently by a CD disk drive (not shown) since digital storage medium 20 is a CD disk. The patient receives unit 10 prepared in this way and is instructed by the physician how and when to play the video game. Of course, the physician may also load several video games at once and instruct the patient when to play each one. Depending on the type of video game and the patient's capabilities, the physician will also determine what patient input device 16 should be employed in playing the game.

The patient takes home unit 10 prepared in this manner, and follows the prescribed treatment by playing the video game. Once in operation, unit 10 displays the graphical video game on display screen 14 and receives input through patient input device 16. The beneficial effect of playing the game is thus available to the patient at any time in his own environment.

The process described above can also be accomplished with the computer network shown in FIG. 2. Here, appropriate treatment programs can be loaded directly into unit 10 used by the patient while he is at home. To do this the physician selects the appropriate video game, determines its destination address, i.e., unit 10, and places the game on hospital network server 28. The designated unit 10 then retrieves the video game via network 26 and loads it into microprocessor 12 and memory 18. This is done with the aid of network link 24 and interface 22.

A particularly convenient method for delivering a video game to the patient is shown in FIG. 3. Hand-held microprocessor unit 30 receives video games directly from hospital computer 52. The video game is transmitted through communication line 44 and received by remote communication unit 42. Unit 42 downloads the game directly into hand-held unit 30 via connection cable 40.

Hand-held unit 30 in FIG. 3 also communicates with clearing house 46 using communication line 44. Thus, the patient's progress in playing the video game can be directly monitored, e.g., by checking the video game scores. This information is screened, classified, and sorted by clearing house 46. Then an abstract or report is transmitted through transmission line 48 to facsimile machine 50 which can be conveniently located in the physician's office.

Unit 30 shown in FIG. 3 can also be used by the patient to check his medical condition. To do this the patient follows instructions embedded in the video game which tell him to connect to unit 30 his measuring device 54, e.g., blood glucose meter in the case of a patient with diabetes. Of course, unit 30 and device 54 may also be hooked up permanently by the physician. Then the video game instructions tell the patient that to continue playing he needs to perform a regular self-measurement using device 54. For a patient with diabetes this involves checking his blood glucose level by drawing a small blood sample into device 54. The individual steps for doing this are not a part of the invention. The measurement data is then downloaded into hand-held unit 30 to be used as input for the interactive video game session. Exemplary video game using this technique to collect data is described in example 4 below. Meanwhile, the blood glucose data is also passed through cable 40 to remote communication unit 42. From there the data follows the same path as described above for the video game score, and can be examined by the physician in the hospital.

The specific examples below describe exemplary microprocessor-based, interactive video games used for treating various medical conditions in human patients.

SMOKING—EXAMPLE 1

Figure 11A:
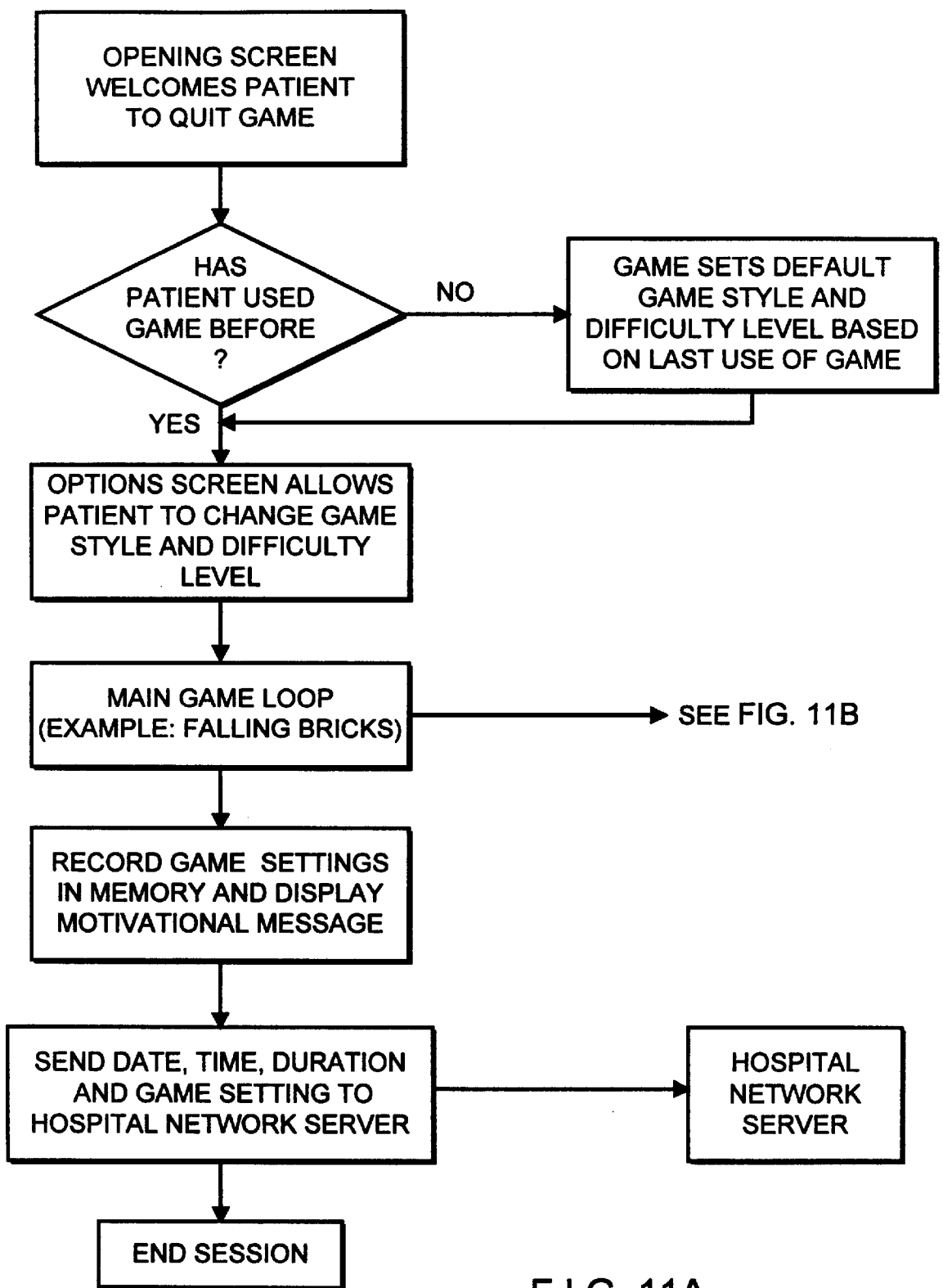
FIG. 11A is a general flowchart of an Addiction/Distraction video game.
Figure 11B:
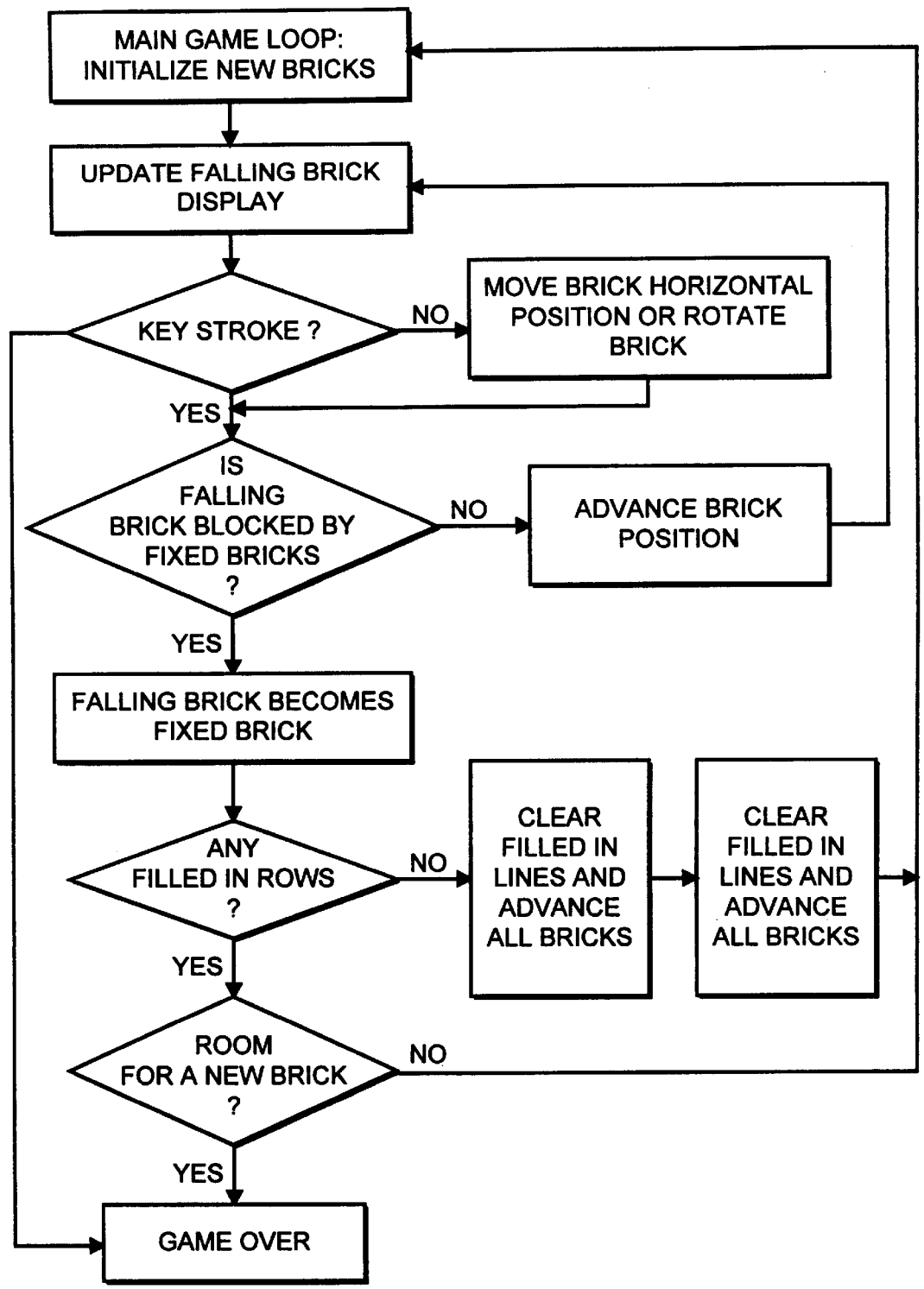
FIG. 11B is a detailed flowchart of the main game loop of the Addiction/Distraction video game shown in FIG. 11A.

The patient has a severe case of nicotine addiction. The physician determines, according to the flow chart in FIG. 4, that distraction is the best psychological strategy to induce the patient to quit smoking. Therefore, the physician prescribes playing the Quit Game, a video game containing a behavioral program based on distraction. This game contains graphical game characters engaging in various competitive activities upon proper input from the user. The smoker plays the game is played whenever he or she feels the urge to smoke. An exemplary game to provide such an engaging distraction is shown in the flowchart illustrated in FIGS. 11A and 11B. In this example, the game is designed to distract the player with falling bricks which have to be arranged in rows. During the game the main characters communicate to the patient instructions and simple strategies to quit smoking immediately and advise the user to take this approach, all within the context of the entertaining video game.

Alternatively, the game provides a timer and timeline for gradual reduction approaches to smoking cessation. Included among these programs are instructions for using nicotine patches. Built in notification will serve to remind smokers to shift to a lower dose patch. Once the smoker has quit, the video game will provide a coping/relapse prevention model by using distraction methods during periods of smoking urges.

A pilot study using the NINTENDO GAME BOY® as a tool to aid smoking cessation was highly successful. In the pilot project, seven smokers were give a Game Boy portable loaded with the Quit Game and instructed to use it any time they felt the urge to smoke. Six of the seven smokers successfully quit and were very enthusiastic about this approach.

An analogous video game strategy is followed in dealing with other substance abuse conditions, alcoholism, and obsessive compulsive disorders.

GROWTH DISORDER—EXAMPLE 2

Figure 12:
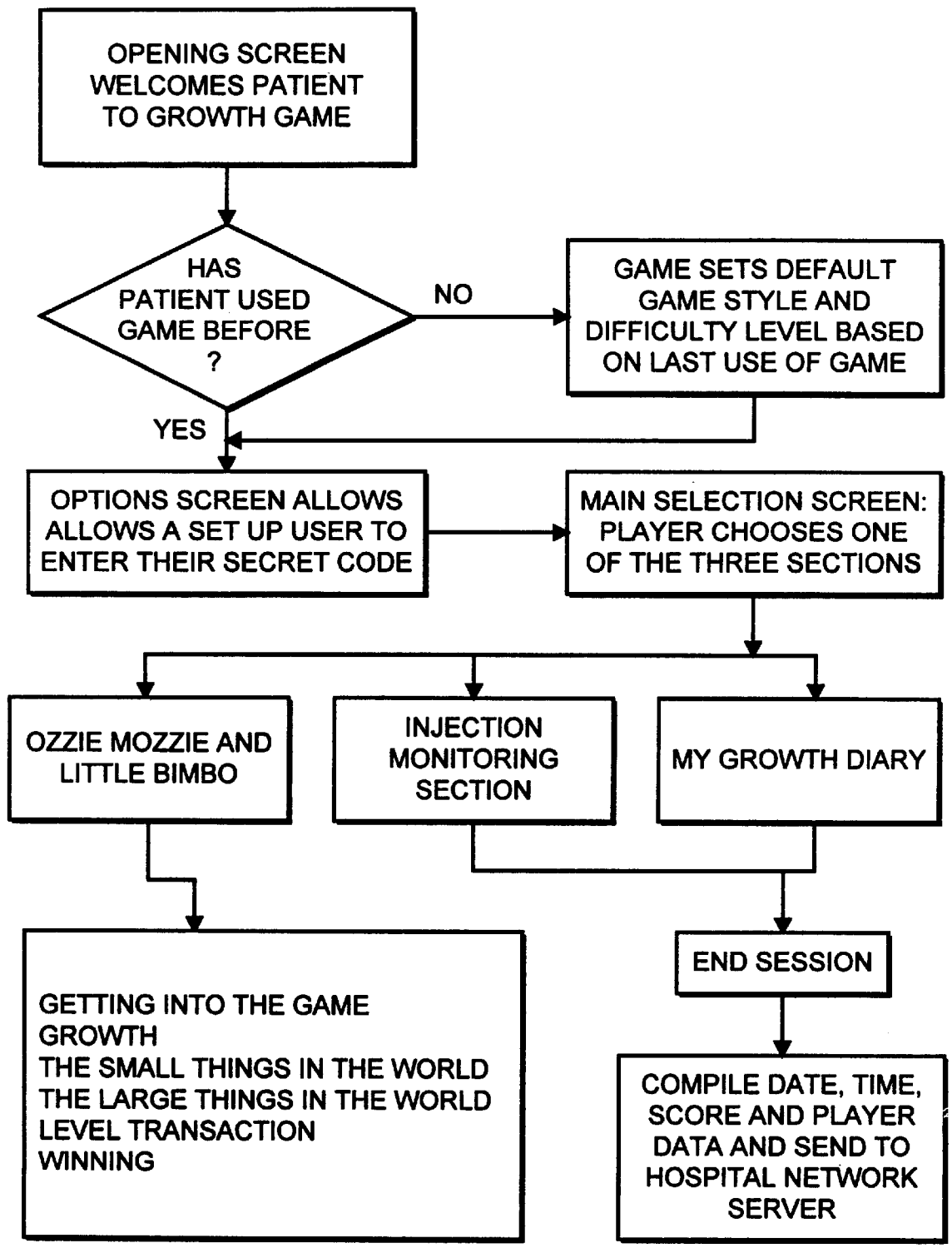
FIG. 12 is a flowchart of the Growth Game.

The physician diagnoses the patient with a growth disorder, such as Turner's Syndrome or a similar condition, requiring growth hormone treatment and a psychological treatment strategy for helping the patient cope with his or her condition. By following a selection process similar to the one indicated in FIG. 4, the physician prescribes a video game combining self-awareness training, self-efficacy, role-playing, counseling and competition. The flowchart for the Growth Game is provided in FIG. 12.

In the video game the graphical game character, Packy, is a young elephant who, like the patient, is on growth hormone therapy. The video game consists of three parts, each associated with a particular aspect of the treatment. In the first part Packy encounters obstacles which he must surmount, in the second he has to learn about growth hormone injections, and in the third one he has to keep a personal growth diary.

Figure 5:
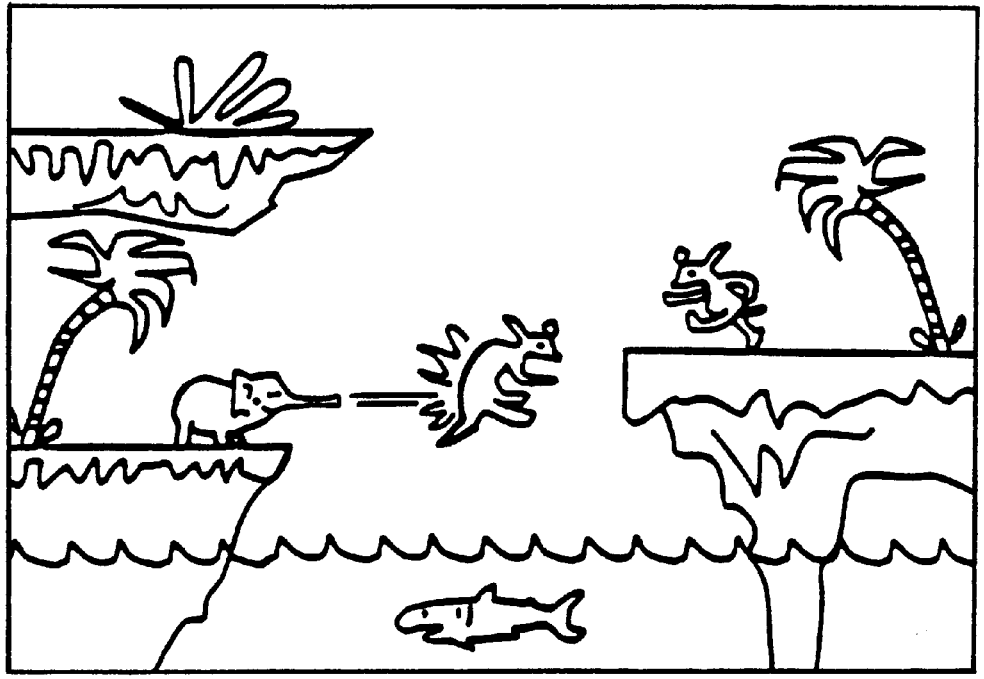
FIG. 5 is an exemplary screen of a video game for treating growth disorders according to the invention.

In the first part Packy learns about things that grow, from the smallest things in the world to the largest ones. In each level of this part Packy can pick up icons of OM (representing a growth hormone shot) for a boost of energy. When he gets this boost, he will grow to a larger size until the energy wears or he gets hit by one of his opponents. Every time Packy meets someone who challenges him he must push them away by pressing a button to lower his head and walking into them, or squirt them by pressing another button. The small antagonists push and squirt away easily, but the large ones require some strategy such as combining pushing and squirting. This stage is depicted in FIG. 5. In each level Packy will occasionally find obstacles that require a growth shot to get past. He will also occasionally encounter a guardian to the pathway that asks him questions from the information learned in the other two parts, i.e., the growth hormone injection instructions and the personal growth diary.

Figure 6:
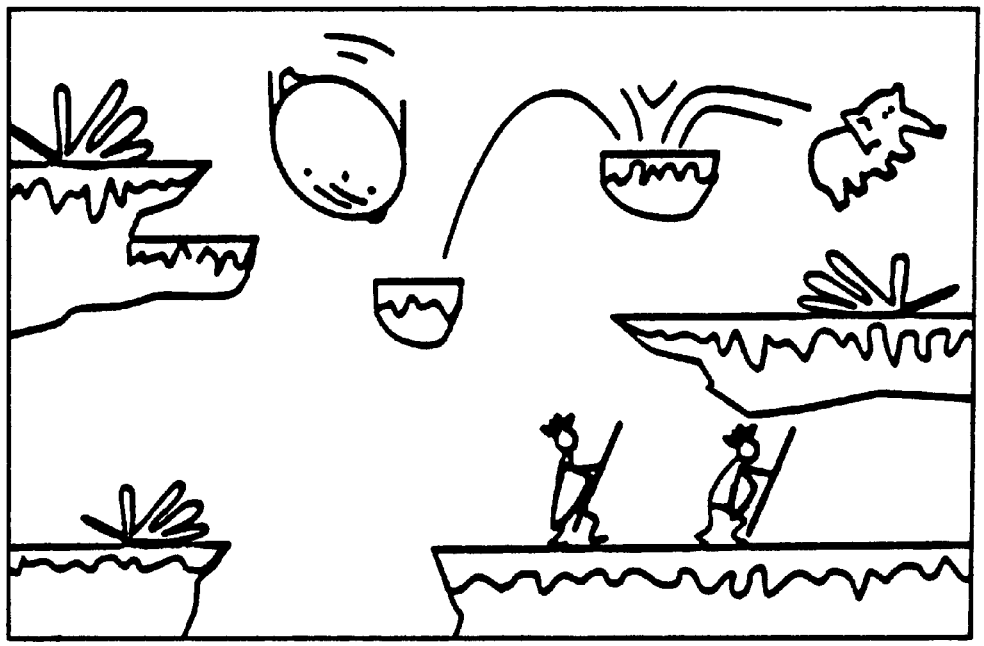
FIG. 6 is another screen of the video game of FIG. 5.

In another level of part one Packy has a dream in which he explores the world as a tiny creature. This scenario is illustrated in FIG. 6. He finds that he is very small himself, while all the surrounding items are very large. As he works his way to the end of this level he will encounter all types of animals and insects that are very small. This level will give Packy a feeling for what it is like to be really small. In the transition to the next level, Packy will wake up and see that he is still the same size, and grateful that he is not so small.

In the final level, Packy finds himself very large. He will be with the giant animals of the world. As he works his way through this level he will encounter all types of animals that are very large and the various types of obstacles they face in daily life. When Packy is bigger than the biggest elephant and cannot enter his home, he begins to realize the problems of being big.

Throughout his quest to feel comfortable with his growth, Packy is accompanied by his mosquito sidekick Zippy. His companion plays the role of a mentor and counsellor throughout the various levels of Packy's adventures.

In part two the patient will learn about preparing and administering doses of growth hormone. First, the user will see how to mix a dose, then prepare a pen for injecting the hormone, and then actually see how an injection is performed. In the game aspect of this part the user will be challenged to mix and administer a dose seven times (Monday through Sunday) and provide accuracy results.

The third part of the game is a growth diary where the patient records and sees various graphics displaying his or her personal progress.

Playing this game is reassuring and helps children overcome growth disorders by emphasizing self-awareness and self-efficacy training, role-playing, competition, and counseling strategies embedded in the video game. Analogous video game strategy is also used to treat anxiety and hyperactivity disorders, various types of phobias, as well as enuresis.

DIABETES—EXAMPLE 3

Figure 7:
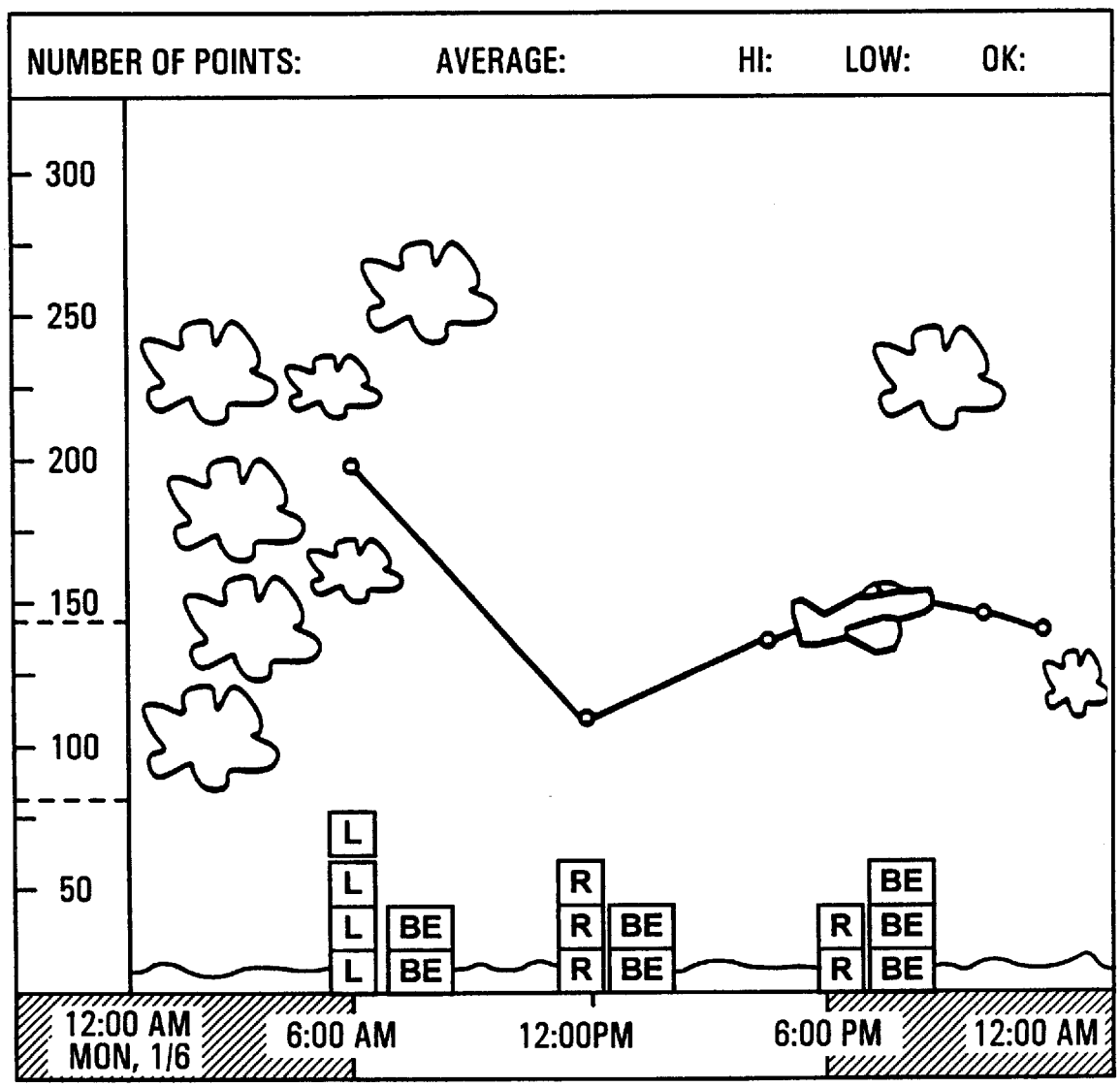
FIG. 7 is an exemplary screen of a video game for diabetes self-treatment according to the invention.
Figure 8:
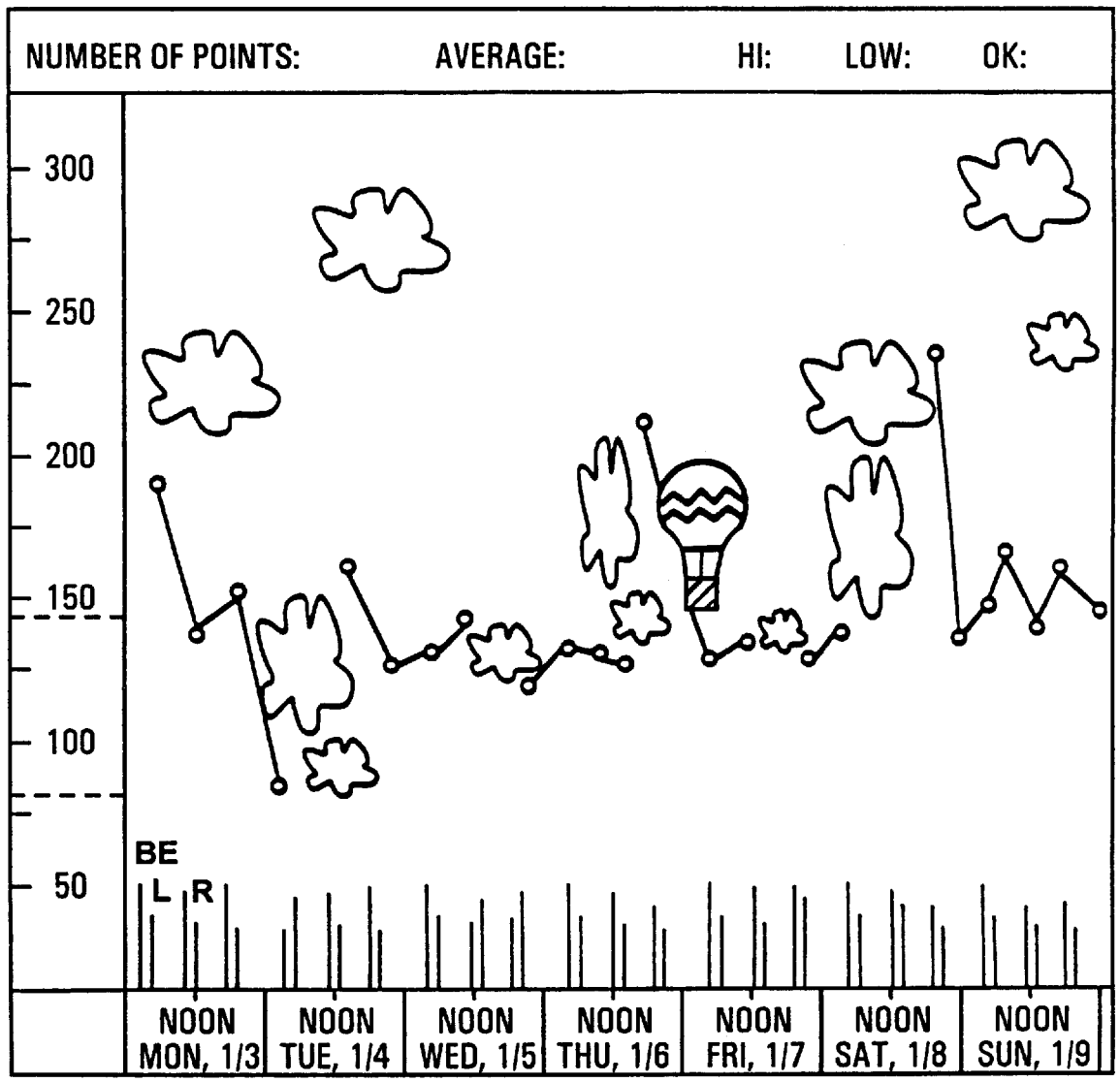
FIG. 8 is another exemplary screen for the video game of FIG. 7.
Figure 13A:
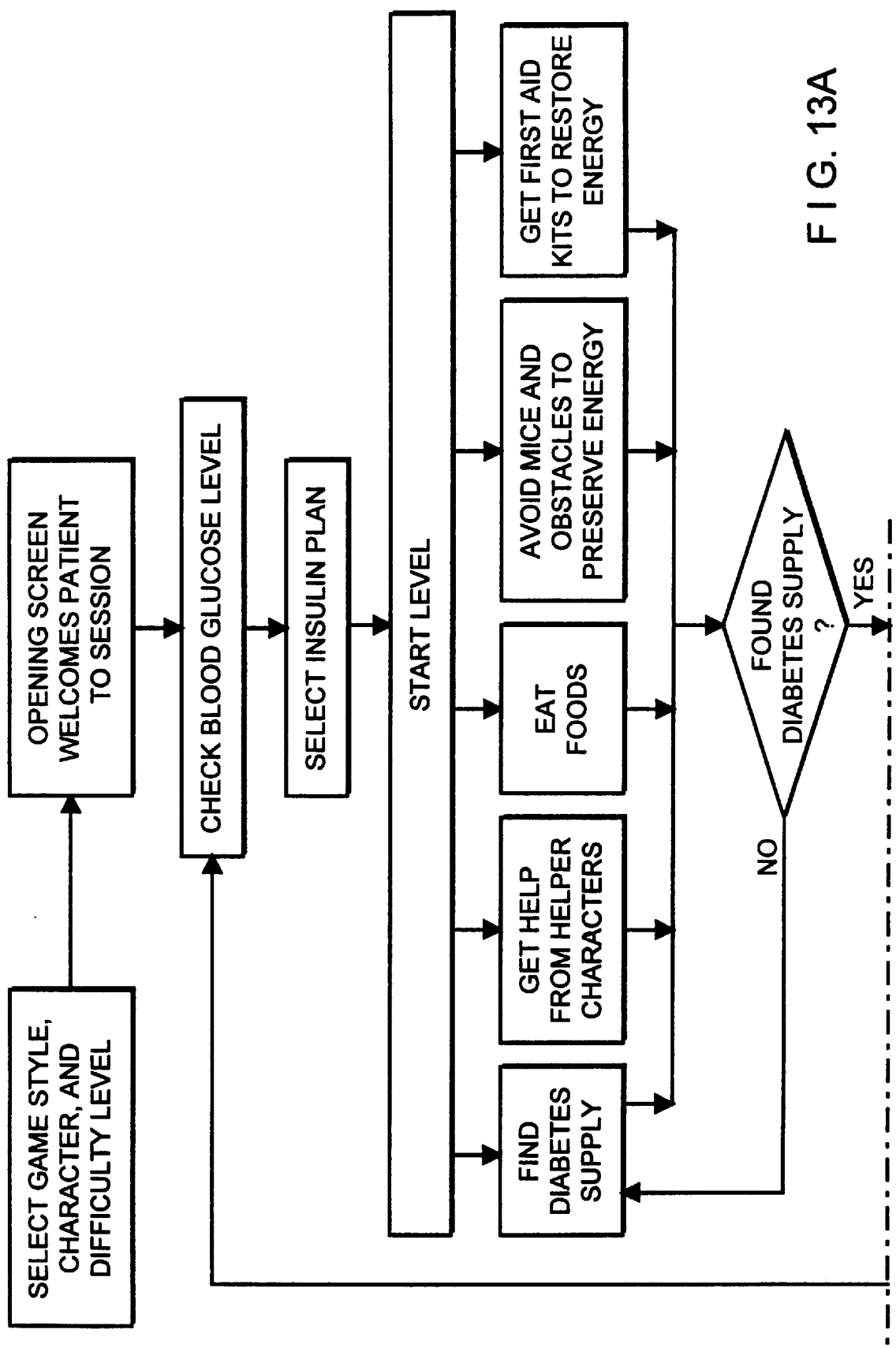
FIG. 13 is a flowchart of an alternative game for measuring blood glucose level.
Figure 13B:
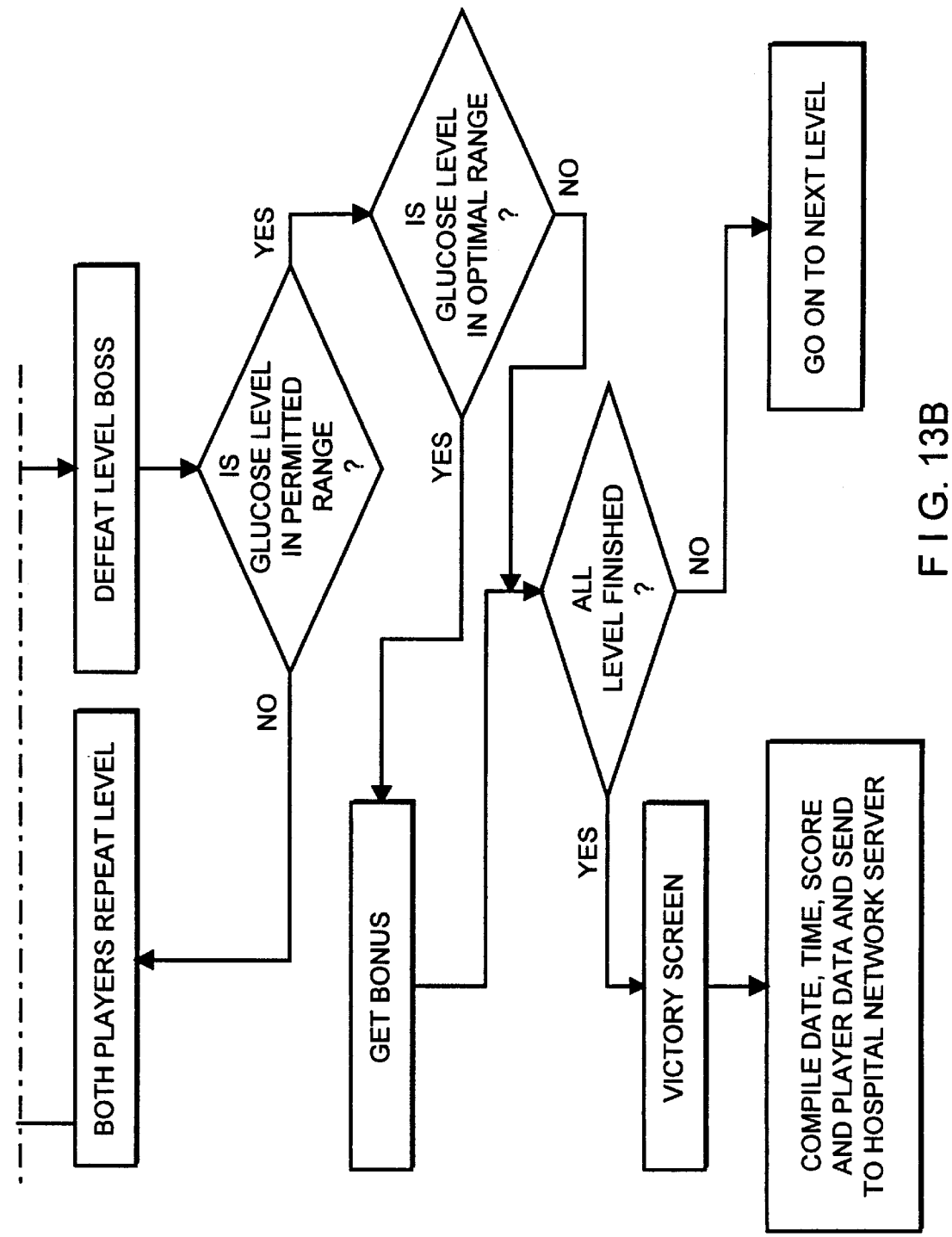

The patient is diagnosed with insulin-dependent diabetes. As treatment the physician prescribes insulin shots and a video game based on positive-reinforcement and self-management. In the video game the graphical game character is a pilot who has diabetes, just like the patient. The pilot needs to follow proper diet and exercise regimen to avoid crashing a plane or balloon which he is flying. The screens for the video game are shown in FIG. 7 and FIG. 8. The flowchart for this games is depicted in FIG. 13. Eating wrong foods causes blood glucose level to increase and the plane or balloon starts gaining altitude uncontrollably. Eventually, above a certain threshold, the balloon or the plane spins out of control.

Figure 10:
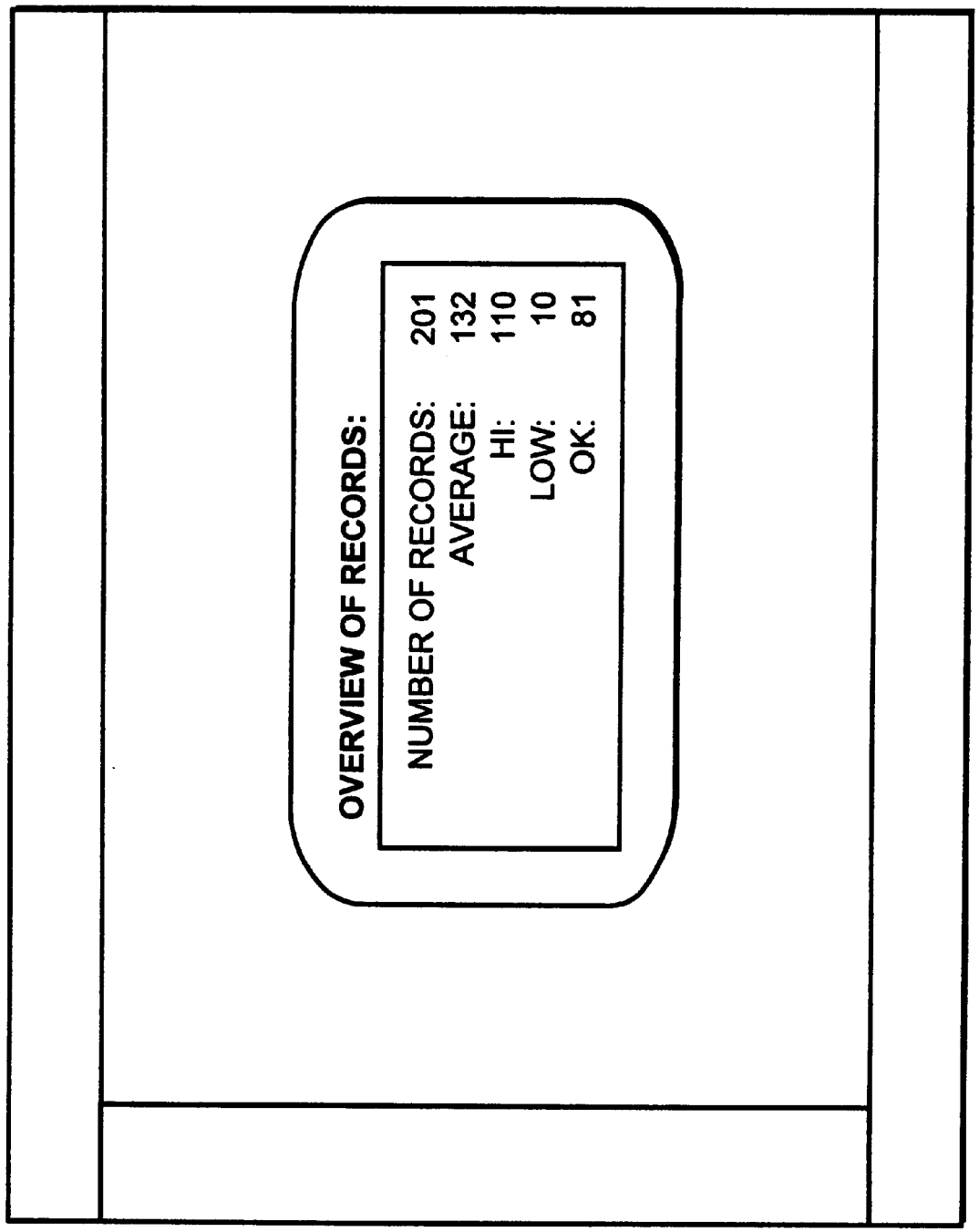
FIG. 10 is a screen indicating the blood glucose measurement results compiled for the video game of FIG. 7.

During the game the patient is requested to enter his own blood glucose level by using blood glucose meter 54. An exemplary set-up for doing this is shown in FIG. 9. The reading is used in the game and can also be transmitted to the hospital, as described in example 3. Also, the user can view his blood glucose readings in the form transmitted to the hospital and used in the game. An example of such reading for a number of measurement records is illustrated in FIG. 10.

If the user does not comply with the request for measuring and entering his blood glucose level the plane or balloon disappears behind clouds, representing uncertainty in blood glucose level. This is visualized by the clouds in FIGS. 7 and 8. The clouds obscure the pilot's vision and lead to collisions with objects in the plane's or balloon's path. Alternatively, if the blood glucose level drops below a minimum threshold, the plane or balloon crashes against the ground.

This positive reinforcement-based strategy, in which the blood glucose level is correlated to a game parameter, e.g., plane altitude, teaches the patient how to cope with his condition on a day-to-day basis while making blood glucose monitoring fun. It also produces higher treatment compliance rates, especially in children who need to learn early on about proper diabetes self-management.

NON-INSULIN DEPENDENT DIABETES MANAGEMENT—EXAMPLE 4

A video game treatment can be used for management of non-insulin dependent cases of diabetes (NIDDM). In such cases the video game is an interactive information resource, as well as a role-playing game. The game helps the patient, especially an adult patient, explore the topic of Staged Diabetes Management. The information is presented in hypertext format, allowing the patient to select a stage, read a brief overview of it, and select details to examine it in greater depth in desired. The game encourages active involvement in learning and provides opportunities to rehearse various health behaviors and see the consequences that result by observing what happens to a graphical game character who displays these behaviors.

The content of the game is based on the Staged Diabetes Management program, developed by the International Diabetes Center and Becton Dickinson & Company. The progressive set of stages ranges from least to most severe. For example, a patient in Stage I will learn to manage NIDDM through diet alone.

In the video game the user can configure the graphical game character in many ways. A checklist of choices allows the patient to combine a variety of physical features and clothes, as well as specifics about the character's health status including weight, age, and medications taken.

The game character, and thus the patient, will make decisions in realistic settings such as restaurants and parties where rich foods are available. Also, an exercise plan will fit in with the character's busy schedule of family, community, and work commitments. This format provides the patient with a playful atmosphere in which choices which the patient faces in his or her own life can be rehearsed.

If blood glucose levels do not remain in the normal range in Stage I, then the patient is instructed by the graphical game character to advance to the next treatment steps, eventually arriving at the stage where the patient will be instructed to inject insulin to control blood glucose levels. The goal of the NIDDM game is to remain at Stage I.

Similar video games can help to deal with hemophilia, and other medical condition requiring the patient to be aware of his or her surroundings.

ASTHMA—EXAMPLE 5

A youngster diagnosed with asthma is given an asthma self-management game for hand-held unit 30. The graphical game character, a young dinosaur from the pre-historic town of San Saurian, must cope with and manage his asthma. The game character confronts common asthma triggers, while learning to recognize early warning signs of an oncoming asthmatic episode. Asthma management techniques including avoidance, relaxation, and medicinal inhalers are part of the daily routine for the young dinosaur who must return to his cave. The dinosaur runs, jumps, and shoots a squirt gun at oncoming triggers while conquering each level and mastering his condition. In addition to these inputs, the dinosaur requests the player to input the player's asthma condition by using physical parameter measuring device 54, which in this case is a respiratory flow meter. These data can then be transmitted to the physician as described above.

Playing the video game involving these real asthma triggers, relaxation techniques, etc., affects the mental state of the player to improve his own asthma management outside of video game sessions. This treatment based on role-playing and positive reinforcement makes the patient aware of the importance of prescribed drugs and teaches appropriate measures for dealing with the patient's condition in real-life situations.

EATING DISORDER—EXAMPLE 6

The physician determines that the patient suffers from an eating disorder causing the patient to gorge. The physician loads into the patient's microprocessor-based unit 10 or hand-held unit 30 a video game in which the graphical game character has to stay thin to survive. The game challenges confronting the game character include avoiding fatty foods to stay trim and eating a sufficient amount to combat dragons and surmount obstacles on his way. Doing this involves making choices about what food presented on the screen to eat, keep for later, or reject. Wrong food choices have immediate consequences in the graphical character's ability to survive. The game is scored according to the length of time the patient is capable of keeping his game character alive and obstacles the character overcomes.

The physician instructs the patient to play the game every time the patient feels an eating urge outside regular meal times. During a regular follow-up visit the doctor evaluates the patient's progress and checks the scores obtained in playing the video game. Based on the analysis of the sores the physician determines the severity of the problem and gets an insight into the patient's motivation to comply with the therapy. Sufficiently high scores reflect progress and readiness to proceed with the next treatment stage. At this point the physician may instruct the patient to play another video game designed for milder eating disorders or a game utilizing a different psychological approach, e.g., negative reinforcement or distraction.

DEPRESSION—EXAMPLE 7

A psychiatrist enrolls a patient in a series of home-based interactive video game sessions, which the patient accesses from his microprocessor-based unit 10 through hospital network 26. The video game is then transmitted from the hospital network server 28 to the patient's unit 10. The game involves interaction with a graphical game character resembling the Yoda character from the popular movie "Star Wars". Yoda acts as a counselor and mentor to the patient, preparing him for various trial episodes in the video game. Based on patient's scores in playing the video game sent, the physician reviews how the patient responds to video game counseling and prepares another game to be transmitted to the patient. This treatment method is part of an on-going therapy for mild to medium-severe depression. This approach is also used for schizophrenia and other purely psychological disorders.

SUMMARY, RAMIFICATIONS, AND SCOPE

The reader will thus see that I have presented a particularly simple method for treating medical conditions in human patients using a microprocessor-based video game. This method gives a better picture of the ailment through its standardized scoring procedure and makes the treatment much less costly by considerably reducing the number of therapy sessions with the physician or health care professional. In addition, video games emphasize superior treatment in the patient's own environment. This leads to self-help responses difficult to foster in therapy sessions. The patient recognizes the importance of medications and treatment regimens in an entertaining manner. Moreover, the patient participates actively in the treatment by following instructions embedded in the video game or even generating positive physiological responses due to stimuli presented in the video game.

The method of the invention also provides a treatment to which the patient can resort as the need arises. The intrinsic fun in playing video games ensures higher treatment compliance for all patients, and in particular children. The self-treatment instructions communicated by this method can be used to additionally induce patients to independently perform measurements of physical parameters associated with their medical condition.

Finally, the scoring of the video game provides an excellent standardized measure for evaluating treatment results and improving continued treatment. In carrying out the method the microprocessor-based system can be expanded to use any number of communications devices, monitoring set-ups, and other state-of-the-art medical equipment. Therefore, the scope of the invention should be determined, not by examples given, but by the appended claims and their legal equivalents.

I claim:

1. In combination in a microprocessor controlled data processing system of the type capable of receiving commands generated by a system user suffering a medical condition, and in response thereto, generating a complex multi-dimensional information display as an output, wherein the output is characterized by the use of indicia on said display configured and presented in a manner directed to the treatment of one or more pre-determined medical conditions, the combination comprising:

means for controlling said data processing system using a stored protocol of display controlling functions wherein said functions include programming commands for controlling one or more graphical elements presented on said display and said protocol is directed to one or more pre-defined medical conditions;

means for storing said programmed protocol in communication with said data processing system;

means for inputting said user generated commands into said data processing system wherein said user generated commands are interactively entered by said system user in response to said output presented on said display; and means for interpreting said inputted user generated commands, applying said stored protocols to said inputted user generated commands and based thereon, controlling said output to said display wherein said output is specifically configured to provide a presentation to said user that enhances the treatment of said medical condition of said system user.

2. The system of claim 1 wherein said combination is a video game wherein said stored protocol of display controlling functions includes programming commands for manipulating at least one graphical character presented on said display and said protocol is directed to allowing said user to overcome challenges related to said pre-defined medical conditions.

3. The system of claim 1 wherein said output comprises a complex scenario that develops a theme, the basis of which enhances treatment of said medical condition.

4. The system of claim 3 wherein said theme includes one or more characters that interact in a manner directly controlled by said user generated commands.

5. The system of claim 4 wherein said characters include a character corresponding, in role playing, to said user.

6. In combination in a microprocessor controlled data processing system capable of generating a complex multi-dimensional information display as a series of outputs and receiving inputs generated by a patient, wherein said series of outputs are characterized by the use of indicia configured and presented in a manner directed to the treatment of one or more pre-determined medical conditions, the combination comprising:

means for storing a programmed protocol of display controlling functions directed to one or more pre-defined medical conditions, wherein said functions comprise programming commands for controlling one or more graphical elements presented on said display and interactive commands for allowing said patient to make said input within a defined parameter of possible inputs, said means for storing in communication with said data processing system;

means for entering said patient generated inputs into said data processing system wherein said patient generated inputs are interactively entered by said patient in response to a first series of outputs presented on said display;

means for applying said stored programmed protocol to said patient generated inputs and based thereon, controlling a second series of outputs to said display wherein said second series of output are specifically configured to provide a presentation to said patient that enhances the treatment of said medical condition of said patient.

7. The system of claim 6 wherein said combination is a video game wherein said stored protocol of display controlling functions includes programming commands for manipulating at least one graphical character presented on said display and said protocol is directed to allowing said user to overcome challenges related to said pre-defined medical conditions.

8. The combination of claim 6 further comprising:

means for linking said system to a network, said linking means comprising a means for interfacing said microprocessor to said network; and at least one peripheral server linked to said network, said server capable of receiving said inputs and said outputs, and capable of exchanging data within said network.

9. The combination of claim 6 further comprising means for directly measuring physiological status of said patient, said measuring means comprised of a second microprocessor controlled data processing system in communication with said combination, wherein said second microprocessor controlled data processing system is capable of exchanging data with said combination.

10. The combination of claim 9 further comprising means for directly measuring physiological status of said patient, said measuring means comprised of a second microprocessor controlled data processing system in communication with said combination, wherein said second microprocessor controlled data processing system is capable of exchanging data within said network.

11. The combination of claim 10, wherein one of said pre-determined medical conditions is diabetes mellitus, said means for directly measuring physiological status of said patient is a blood glucose meter, and said network links said patient to at least one terminal controlled by a health care professional.

12. The combination of claim 6, wherein said programmed protocol of display controlling functions comprise programming commands for controlling graphical elements presented on said display, said graphical elements selected from the group consisting of those providing education, distraction, compliance structure, record maintenance and role play.

13. The combination of claim 12, wherein said graphical elements providing education contribute information and positive reinforcement to said patient on one or more said pre-determined medical conditions.

14. The combination of claim 12, wherein said graphical elements for distraction provide support measures to reduce urges selected from those cravings for alcohol, tobacco, food and DEA contolled substances.

* * * * *